United States Patent [19]

Chen et al.

[11] Patent Number: 5,256,391
[45] Date of Patent: Oct. 26, 1993

[54] METHOD FOR SYNTHESIZING MICROPOROUS CRYSTALLINE MATERIAL

[75] Inventors: Catherine S. H. Chen, Berkeley Heights; John L. Schlenker, Pennington; Steven E. Wentzek, East Brunswick, all of N.J.

[73] Assignee: Mobil Oil Corporation, Fairfax, Va.

[21] Appl. No.: 943,644

[22] Filed: Sep. 11, 1992

[51] Int. Cl.$^5$ .............................................. C01B 33/34
[52] U.S. Cl. ...................................... 423/706; 423/328.1
[58] Field of Search ..................... 423/706, 707, 328.1

[56] References Cited

U.S. PATENT DOCUMENTS

| | | | |
|---|---|---|---|
| 4,657,748 | 4/1987 | Vaughan et al. | 423/707 |
| 4,665,110 | 5/1987 | Zones | 423/706 |
| 4,826,667 | 5/1989 | Zones et al. | 423/706 |
| 4,834,958 | 5/1989 | Zones et al. | 423/706 |
| 4,859,442 | 8/1989 | Zones et al. | 423/706 |

*Primary Examiner*—R. Bruce Breneman
*Attorney, Agent, or Firm*—Alexander J. McKillop; Dennis P. Santini; Robert B. Furr, Jr.

[57] ABSTRACT

The invention provides a method for synthesizing a porous inorganic solid comprising the steps of: (a) forming a reaction mixture containing water, an alumina source, a silica source, an alkali metal oxide source, and a diquaternary ammonium salt having the formula:

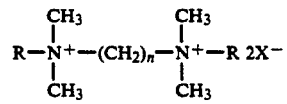

wherein R is a diamondoid group, n is from about 1 to about 50, and X is an anion which is not detrimental to the formation of said porous inorganic solid; and
 (b) recovering a porous inorganic solid from said reaction mixture.

12 Claims, No Drawings

METHOD FOR SYNTHESIZING MICROPOROUS CRYSTALLINE MATERIAL

FIELD OF THE INVENTION

This invention relates to the synthesis of inorganic porous solids. More specifically, this invention provides a method for synthesizing crystalline microporous materials which requires no added nucleating seeds in the reaction mixture.

BACKGROUND OF THE INVENTION

Porous inorganic solids have found great utility as catalysts and separations media for industrial application. The openness of their microstructure allows molecules access to the relatively large surface areas of these materials that enhance their catalytic and sorptive activity. The porous materials in use today can be sorted into three broad categories using the details of their microstructure as a basis for classification. These categories are the amorphous and paracrystalline supports, the crystalline molecular sieves and modified layered materials. The detailed differences in the microstructures of these materials manifest themselves as important differences in the catalytic and sorptive behavior of the materials, as well as in differences in various observable properties used to characterize them, such as their surface area, the sizes of pores and the variability in those sizes, the presence or absence of X-ray diffraction patterns and the details in such patterns, and the appearance of the materials when their microstructure is studied by transmission electron microscopy and electron diffraction methods.

Amorphous and paracrystalline materials represent an important class of porous inorganic solids that have been used for many years in industrial applications. Typical examples of these materials are the amorphous silicas commonly used in catalyst formulations and the paracrystalline transitional aluminas used as solid acid catalysts and petroleum reforming catalyst supports. The term "amorphous" is used here to indicate a material with no long range order and can be somewhat misleading, since almost all materials are ordered to some degree, at least on the local scale. An alternate term that has been used to describe these materials is "X-ray indifferent". The microstructure of the silicas consists of 100-250 Angstrom particles of dense amorphous silica (*Kirk-Othmer Encyclopedia of Chemical Technology*, 3rd Edition, Vol. 20, John Wiley & Sons, New York, p. 766-781, 1982), with the porosity resulting from voids between the particles. Since there is no long range order in these materials, the pores tend to be distributed over a rather large range. This lack of order also manifests itself in the X-ray diffraction pattern, which is usually featureless.

Paracrystalline materials such as the transitional aluminas also have a wide distribution of pore sizes, but better defined X-ray diffraction patterns usually consisting of a few broad peaks. The microstructure of these materials consists of tiny crystalline regions of condensed alumina phases and the porosity of the materials results from irregular voids between these regions (K. Wefers and Chanakya Misra, "Oxides and Hydroxides of Aluminum", Technical Paper No. 19 Revised, Alcoa Research Laboratories, p. 54-59, 1987). Since, in the case of either material, there is no long range order controlling the sizes of pores in the material, the variability in pore size is typically quite high. The sizes of pores in these materials fall into a regime called the mesoporous range, which, for the purposes of this application, is from about 13 to 200 Angstroms.

In sharp contrast to these structurally ill-defined solids are materials whose pore size distribution is very narrow because it is controlled by the precisely repeating crystalline nature of the materials' microstructure. These materials are called "molecular sieves", the most important examples of which are zeolites.

Zeolites, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials are known as "molecular sieves" and are utilized in a variety of ways to take advantage of these properties.

Such molecular sieves, both natural and synthetic, include a wide variety of positive ion-containing crystalline silicates. These silicates can be described as a rigid three-dimensional framework of $SiO_4$ and Periodic Table Group IIIB element oxide, e.g. $AlO_4$, in which the tetrahedra are cross-linked by the sharing of oxygen atoms whereby the ratio of the total Group IIIB element, e.g. aluminum, and Group IVB element, e.g. silicon, atoms to oxygen atoms is 1:2. The electrovalence of the tetrahedra containing the Group IIIB element, e.g. aluminum, is balanced by the inclusion in the crystal of a cation, for example, an alkali metal or an alkaline earth metal cation.

This can be expressed wherein the ratio of the Group IIIB element, e.g. aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite A (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); zeolite ZSM-12 (U.S. Pat. No. 3,832,449); zeolite ZSM-20 (U.S. Pat. No. 3,972,983); ZSM-35 (U.S. Pat. No. 4,016,245); and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724; 4,073,865 and 4,104,294 describe crystalline silicate of varying alumina and metal content.

Aluminum phosphates are taught in U.S. Pat. Nos. 4,310,440 and 4,385,994, for example. These aluminum phosphate materials have essentially electroneutral lattices. U.S. Pat. No. 3,801,704 teaches an aluminum phosphate treated in a certain way to impart acidity.

An early reference to a hydrated aluminum phosphate which is crystalline until heated at about 110° C., at which point it becomes amorphous or transforms, is the "$H_1$" phase or hydrate of aluminum phosphate of F.d'Yvoire, *Memoir Presented to the Chemical Society*, No. 392, "Study of Aluminum Phosphate and Trivalent Iron", Jul. 6, 1961 (received), pp. 1762–1776. This material, when crystalline, is identified by the JCPDS International Center for Diffraction Data card number 15-274. Once heated at about 110° C., however, the d'Yvoire material becomes amorphous or transforms to the aluminophosphate form of tridymite.

Compositions comprising crystals having a framework topology after heating at 110° C. or higher giving an X-ray diffraction pattern consistent with a material having pore windows formed by 18 tetrahedral members of about 12–13 Angstroms in diameter are taught in U.S. Pat. No. 4,880,611.

A naturally occurring, highly hydrated basic ferric oxyphosphate mineral, cacoxenite, is reported by Moore and Shen, Nature, Vol. 306, No. 5941, pp. 356–358 (1983) to have a framework structure containing very large channels with a calculated free pore diameter of 14.2 Angstroms. R. Szostak et al., *Zeolites: Facts, Figures, Future*, Elsevier Science Publishers B.V., 1989, present work showing cacoxenite as being very hydrophilic, i.e. adsorbing non-polar hydrocarbons only with great difficulty. Their work also shows that thermal treatment of cacoxenite causes an overall decline in X-ray peak intensity.

Silicoaluminophosphates of various structures are taught in U.S. Pat. No. 4,440,871. Aluminosilicates containing phosphorous, i.e. silicoaluminophosphates of particular structures are taught in U.S. Pat. Nos. 3,355,246 (i.e. ZK-21) and 3,791,964 (i.e. ZK-22). Other teachings of silicoaluminophosphates and their synthesis include U.S. Pat. Nos. 4,673,559 (two-phase synthesis method); 4,623,527 (MCM-10); 4,639,358 (MCM-1); 4,647,442 (MCM-2); 4,664,897 (MCM-4); 4,638,357 (MCM-5); and 4,632,811 (MCM-3).

A method for synthesizing crystalline metalloaluminophosphates is shown in U.S. Pat. Nos. 4,713,227, and an antimonophosphoaluminate and the method for its synthesis are taught in U.S. Pat. No. 4,619,818. U.S. Pat. No. 4,567,029 teaches metalloaluminophosphates, and titaniumaluminophosphate and the method for its synthesis are taught in U.S. Pat. No. 4,500,651.

The phosphorus-substituted zeolites of Canadian Patents 911,416; 911,417; and 911,418 are referred to as "aluminosilicophosphate" zeolites. Some of the phosphorus therein appears to be occluded, not structural.

U.S. Pat. No. 4,363,748 describes a combination of silica and aluminum-calcium-cerium phosphate as a low acid activity catalyst for oxidative dehydrogenation. Great Britain Patent 2,068,253 discloses a combination of silica and aluminum-calcium-tungsten phosphate as a low acid activity catalyst for oxidative dehydrogenation. U.S. Pat. No. 4,228,036 teaches an alumina-aluminum phosphate-silica matrix as an amorphous body to be mixed with zeolite for use as cracking catalyst. U.S. Pat. No. 3,213,035 teaches improving hardness of aluminosilicate catalysts by treatment with phosphoric acid. The catalysts are amorphous.

Other patents teaching aluminum phosphates include U.S. Pat. Nos. 4,365,095; 4,361,705; 4,222,896; 4,210,560; 4,179,358; 4,158,621; 4,071,471; 4,014,945; 3,904,550; and 3,697,550.

The precise crystalline microstructure of most zeolites manifests itself in a well-defined X-ray diffraction pattern that usually contains many sharp maxima and that serves to uniquely define the material. Similarly, the dimensions of pores in these materials are very regular, due to the precise repetition of the crystalline microstructure. All molecular sieves discovered to date have pore sizes in the microporous range, which is usually quoted as 2 to 20 Angstroms, with the largest reported being about 12 Angstroms.

Certain layered materials, which contain layers capable of being spaced apart with a swelling agent, may be pillared to provide materials having a large degree of porosity. Examples of such layered materials include clays. Such clays may be swollen with water, whereby the layers of the clay are spaced apart by water molecules. Other layered materials are not swellable with water, but may be swollen with certain organic swelling agents such as amines and quaternary ammonium compounds. Examples of such non-water swellable layered materials are described in U.S. Pat. No. 4,859,648 and include layered silicates, magadiite, kenyaite, trititanates and perovskites. Another example of a non-water swellable layered material, which can be swollen with certain organic swelling agents, is a vacancy-containing titanometallate material, as described in U.S. Pat. No. 4,831,006.

Once a layered material is swollen, the material may be pillared by interposing a thermally stable substance, such as silica, between the spaced apart layers. The aforementioned U.S. Pat. Nos. 4,831,006 and 4,859,648 describe methods for pillaring the non-water swellable layered materials described therein and are incorporated herein by reference for definition of pillaring and pillared materials.

Other patents teaching pillaring of layered materials and the pillared products include U.S. Pat. Nos. 4,216,188; 4,248,739; 4,176,090; and 4,367,163; and European Patent Application 205,711.

The X-ray diffraction patterns of pillared layered materials can vary considerably, depending on the degree that swelling and pillaring disrupt the otherwise usually well-ordered layered microstructure. The regularity of the microstructure in some pillared layered materials is so badly disrupted that only one peak in the low angle region on the X-ray diffraction pattern is observed, as a d-spacing corresponding to the interlayer repeat in the pillared material. Less disrupted materials may show several peaks in this region that are generally orders of this fundamental repeat. X-ray reflections from the crystalline structure of the layers are also sometimes observed. The pore size distribution in these pillared layered materials is narrower than those in amorphous and paracrystalline materials but broader than that in crystalline framework materials.

The synthetic porous inorganic materials are generally produced from a reaction mixture (or "gel") which contains the precursors of the synthetic material. Because the necessary seed crystals may be unavailable (particularly when the porous inorganic material is new and has not previously been synthesized) it would be desirable to provide a synthesis method which generates a selected porous inorganic material from a particular reaction mixture containing no nucleating seeds.

The reaction mixture for a particular porous inorganic material may also contain an organic directing agent or templating agent. The terms "templating agent" and "directing agent" are both used to describe compounds (usually organics) added to the reaction mixture to promote formation of the desired porous inorganic solid.

Bulky organic bases which are favored as directing agents include cetyltrimetylammonium (CTMA), myristyltrimethylammonium ($C_{14}$TMA), decyltrimethylammonium, cetyltrimethylphosphonium, octadecyltrimethylphosphonium, benzyltrimethylammonium, cetylpyridinium, dodecyltrimethylammonium, and dimethyldidodecylammonium, merely to name a few. The templating action of various organic entitles is also discussed in A. Dyer *An Introduction to Zeolite Molecular Sieves* 60 (1988), as well as in B. M. Lok et al., The Role of Organic Molecules in Molecular Sieve Synthesis 3 Zeolites 282 (1983), which are incorporated by reference as if set forth at length herein. These materials are costly, and usually account for most of the materials-related expense in the synthesis of inorganic porous solids.

U.S. Pat. No. 4,665,110 to Zones teaches a process for preparing molecular sieves using an adamantane-derived template. U.S. Pat. No. 4,826,667 to Zones teaches a method for making zeolite SSZ-25 using an adamantane quaternary ammonium ion as a template.

U.S. Pat. No. 4,657,748 to Vaughan and Strohmaier discloses the zeolite ECR-1. For a discussion of a proposed structure of zeolite ECR-1, see M. E. Leonowicz and D. E. W. Vaughan, "Proposed synthetic zeolite ECR-1 structure gives a new zeolite framework topology", Nature, Vol. 329, No. 6142, pages 819–821 (Oct., 1987).

Adamantane, tricyclo-[3.3.1.1.$^{3,7}$]decane, is a polycyclic alkane with the structure of three fused cyclohexane rings. The ten carbon atoms which define the framework structure of adamantane are arranged in an essentially strainless manner. Four of these carbon atoms, the bridgehead carbons, are tetrahedrally disposed about the center of the molecule. The other six (methylene carbons) are octahedrally disposed. U.S. Pat. Nos. 5,019,660 to Chapman and Whitehurst and 5,053,434 to Chapman teach diamondoid compounds which bond through the methylene positions of various diamondoid compounds, including adamantane. For a survey of the chemistry of diamondoid molecules, see *Adamantane, The Chemistry of Diamond Molecules*, Raymond C. Fort, Marcel Dekker, New York, 1976.

Adamantane has been found to be a useful building block in the synthesis of a broad range of organic compounds.

Many hydrocarbonaceous mineral streams contain some small proportion of diamondoid compounds. These high boiling, saturated, three-dimensional polycyclic organics are illustrated by adamantane, diamantane, triamantane and various side chain substituted homologues, particularly the methyl derivatives. These compounds have high melting points and high vapor pressures for their molecular weights and have recently been found to cause problems during production and refining of hydrocarbonaceous minerals, particularly natural gas, by condensing out and solidifying, thereby clogging pipes and other pieces of equipment.

In recent times, new sources of hydrocarbon minerals have been brought into production which, for some unknown reason, have substantially larger concentrations of diamondoid compounds. Whereas in the past, the amount of diamondoid compounds has been too small to cause operational problems such as production cooler plugging, now these compounds represent both a larger problem and a larger opportunity. The presence of diamondoid compounds in natural gas has been found to cause plugging in the process equipment requiring costly maintenance downtime to remove. On the other hand, these very compounds which can deleteriously affect the profitability of natural gas production are themselves valuable products.

The problem of deposition and plugging by solid diamondoids in natural gas production equipment has been successfully addressed by a controlled solvent injection process. U.S. Pat. No. 4,952,748 to Alexander and Knight teaches the process for extracting diamondoid compounds from a hydrocarbon gas stream by contacting the diamondoid-laden hydrocarbon gas with a suitable solvent to preferentially dissolve the diamondoid compounds into the solvent. U.S. Pat. No. 5,120,899 to Chen and Wentzek teaches a particularly useful method for sorbing and isolating diamondoid fractions.

Further studies have revealed that separation of the diamondoid compounds from the diamondoid-enriched solvent is complicated by the fact that numerous diamondoid compounds boil in a narrow range of temperatures surrounding the boiling range of the most preferred solvents. U.S. Pat. Nos. 4,952,747, 4,952,749, and 4,982,049 to Alexander et al. teach various methods of concentrating diamondoid compounds in the solvent for, among other reasons, recycling the lean solvent fraction for reuse. Each of these processes produces an enriched solvent stream containing a mixture of diamondoid compounds.

The above-listed U.S. Patents are incorporated by reference as if set forth at length herein for the details of recovering and concentrating diamondoid compounds.

Thus it would be beneficial to (a) provide an economical directing agent; (b) convert a now abundant supply of diamondoids into valuable fine chemicals; and (c) provide a method for synthesizing porous inorganic compounds in the absence of nucleating seeds.

SUMMARY OF THE INVENTION

The present invention is directed to an improved method for synthesis of a porous inorganic solid comprising forming a reaction mixture containing water, an alumina source, a silica source, an alkali metal oxide source, and a diquaternary ammonium salt having the formula

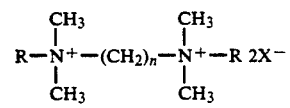

wherein R is a diamondoid group and n is from about 1 to about 50, preferably from about 1 to about 20, more preferably from about 2 to about 12, most preferably from about 3 to about 10, and wherein X is an anion which is not detrimental to the formation of the porous inorganic solid, and is preferably a halogen or hydroxide, more preferably $I^-$. R preferably comprises one member of the group consisting of adamantane, diamantane, and triamantane, and more preferably comprises adamantane. Reaction temperature may range from below ambient to about 400° C., and temperatures of from about 120° to about 180° C. are preferred for crystallization of the zeolite ECR-1.

In one embodiment, the reaction mixture is further characterized by the following approximate molar ratios of oxides:

| | |
|---|---|
| $SiO_2/Al_2O_3$: | 10 to 80 |
| $OH^-/SiO_2$: | 0.50 (fixed) |
| $H_2O/SiO_2$: | 30 to 90 |
| $R/SiO_2$: | 0.05 to 0.10 |
| $Na^+/SiO_2$: | 0.54 (fixed) |

The synthesis method of the invention functions with or without added nucleating seeds. In a preferred embodiment, the reaction mixture of the invention contains no nucleating seeds. The porous inorganic solid synthesized in accordance with the invention is preferably a crytalline microporous material.

The term "diamondoid" is used in its usual sense, i.e., to designate the family of polycyclic alkanes exemplified by adamantane, diamantane, and triamantane and their substituted and functionalized homologs.

The invention further includes a method for the quaternization of diamondoid-substituted tertiary amino groups comprising the steps of dissolving the diamondoid-substituted tertiary amine in dimethylformamide, adding anhydrous sodium carbonate to said dimethylformamide solution, and adding excess methyl iodide to the sodium carbonate-containing dimethylformamide mixture.

The new templates and the specific conditions using these templates as disclosed herein facilitate the crystallization of ECR-1 as well as other unidimensional large pore zeolites. These templates by no means resemble those used in U.S. Pat. No. 4,657,748 for the formation of ECR-1, and the discovery that they nucleate the crystallization of ECR-1 is unexpected. In addition, no nucleating seed was required using these templates to produce ECR-1. In the ECR-1 synthesis set forth in U.S. Pat. No. 4,657,748, the template used was a bis-(2-hydroxyalky) dimethylammonium chloride. In addition, sodium zeolite (aluminosilicate) nucleating seeds were required for the crystallization. In the synthesis of the present invention, the crystallization proceeds without adding sodium zeolite seeds. Further, the ECR-1 samples synthesized in accordance with the present invention showed useful catalytic activity as evidenced by the observed high Alpha values.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of silica-alumina cracking catalyst taken as an Alpha of 1 (Rate Constant=0.016 $sec^{-1}$). The Alpha Test is described in U.S. Pat. No. 3,354,078; in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, vol. 61, p. 395.

The synthesis process of the invention hydrothermally produces ECR-1 crystals at a $SiO_2/Al_2O_3$ feed ration of 10–40, and at temperatures between 120°-160° C. At a $SiO_2/Al_2O_3$ ratio of about 10, the ECR-1 product formed has a $SiO_2/Al_2O_3$ ratio of 7.5, and can contain minor amounts of Analcime. At a $SiO_2/Al_2O_3$ feed ratio of about 40, the zeolite product has a $SiO_2/Al_2O_3$ ratio of about 15 and contains a mixture of ECR-1 and mordenite. At a $SiO_2/Al_2O_3$ feed ratio of about 80, the zeolite product has a $SiO_2/Al_2O_3$ ratio of about 30 and contains essentially mordenite. The synthesis method of the invention produces essentially pure ECR-1 product using a $SiO_2/Al_2O_3$ feed ratio of from about 10 to about 20. The as-synthesized zeolites are stable to calcination at 538° C. in nitrogen followed by calcination in air.

In accordance with the present invention, ECR-1 can be synthesized hydrothermally using the above adamantane-containing diquarternary ammonium iodides (where n is from about 6 to about 9) as templates. The preferred aluminum source is $NaAlO_2$, while the preferred silicon source is $SiO_2$ sol (30% $SiO_2$ in $H_2O$), which is commercially available as Catalog No. SX0140-1 from EM Science, Inc.

Embodiments Synthesis of the Directing Agent

The directing agent of the present invention may suitably be synthesized in accordance with the following general procedure which includes the sequential steps of: (1) imine formation between 2-adamantanone and a primary amine, (2) hydrogenation of the imine to the secondary amine, (3) methylation to the tertiary amine and (4) quaternization with methyl iodide. The overall yield to the tertiary amine is typically 90% or higher. By combining steps (1) and (2) and carrying out a reductive amination, the synthesis can start with a secondary amine and produce a tertiary amine directly and with similar high yield. Although the quaternization of adamantyl substituted tertiary amines requires more drastic conditions than the usual mild conditions employed in quaternizations, it typically produces 90% or higher yields from the tertiary amines in HPLC grade dimethylformamide in a pressure vessel. By this route, the directing agent synthesis of the invention has produced a variety of novel adamantane-containing amines and quaternary ammonium salts of different sizes, shapes, and charge densities. These quaternary ammonium salts are useful as nucleating agents for syntheses of zeolites and other porous catalysts, as well as for pharmeceutical applications as antivirals.

The directing agent may be synthesized in accordance with the following procedure:

(1) Imine formation between 2-adamantanone and a primary amine: the imine formation was carried out in an appropriate solvent which formed an azeotrope with water to displace the following equilibrium to the right:

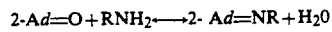

The reaction was carried out in a flask equipped with a mechanical stirrer, a Dean-Stark trap, and a condenser. In general, the reaction was complete in about four hours as evidenced by the calculated amount of water collected in the Dean-Stark trap. When there were more than one primary amino group present in the reactant amine, toluene was used as the solvent because these amines typically had high boiling points. To ensure all the amino groups were to be reacted, a 10% mole excess 2-adamantanone was employed. After the reaction the toluene was distilled off and the excess 2-adamantanone was removed by sublimation under vacuum. In cases where the amines contained only one primary amino group and were relatively low boiling, cyclohexane was used as the solvent to azeotrope out the produced water, and the amine was used in 20% mole excess. The pot temperature was kept below the boiling point of the amine to prevent the amine from distilling off. After reaction was complete, both cyclohexane and the excess amine were removed by distillation. The structures of the imine products were established by C-13 NMR. The yield based on the reactant not in excess was generally near quantitative.

(2) Hydrogenation of Imines to Secondary Amines: The hydrogenation was carried out in ethanol using Pd/C as the catalyst at 50° C. or Ni/Kieselgel as the catalyst at 100° C. Complete hydrogenation took 48-72 hours. The hydrogenated products were generally crystalline or crystallizable from ethanol. The structures of the secondary amines were confirmed by C-13 NMR. The yield from the imine was generally quantitative.

(3) Methylation of Secondary to Tertiary Amine: The methylation step was carried out in accordance with the following general procedure. For a discussion of methylation, see H. W. Geluk and V. G. Keiser, Org. Synthesis, 53, 8, 1973. One mole of a secondary amino group (in these Examples, a molecule often contained more than one secondary amino group) was added slowly to 2.5 moles formic acid (96% in water) in a 2-neck flask equipped with an air-driven mechanical stirrer and a water condenser. Upon stirring, 1.1 moles of formaldehyde (37% in water) were added slowly, followed by the addition of 100 ml water. The mixture was slowly heated to reflux. The solid amine went into solution and gas ($CO_2$) was evolved. The mixture was refluxed overnight until the gas evolution had ceased. Upon cooling, an amount of 195 ml concentrated HCl (36%) was added slowly and the excess formaldehyde and formic acid were driven off at boiling with mechanical stirring while bubbling through a stream of nitrogen. The mixture was cooled down and neutralized with 25% sodium hydroxide solution. The tertiary amine formed was then extracted with ether. The ether extract was washed with water and dried over anhydrous magnesium sulfate. After filtration the ether was distilled off to recover the tertiary amine product. The structure of the product was characterized by C-13 NMR. Yield in this methylation step averaged 90%.

(4) Quaternization: Quaternization of tertiary amino groups, without an adamantyl substituent, required mild conditions under which the adamantyl substituted amino groups are not affected, and was achieved by slowly dropping methyl iodide into an ethanol solution of the amine keeping the temperature under 35° C. The product precipitated out as a solid.

The quaternization of adamantyl substituted tertiary amino groups required more stringent conditions. The presence of any protonic compound either as a solvent or as an impurity resulted in the formation of proton ammonium instead of quaternary ammonium salts. The best solvent was discovered to be HPLC grade (pure) dimethylformamide which was syringed directly into the quaternization reactor to avoid possible exposure to moisture. It was also found to be advantageous to add to the reaction a small amount of anhydrous sodium carbonate. Excess methyl iodide, at a mole ratio of 1.5 $CH_3I$ to 1 amino group and an elevated temperature (60°-90° C.) were required. Due to the low boiling point of $CH_3I$, the reactions were carried out in a Parr reactor. The yield of the quaternization was as high as 90%; however, in some cases other parts of the molecule could degrade (see the following Examples II and III) rendering the overall yield significantly lower.

The following Examples 1-5 illustrate the synthesis of diquaternary amines useful as directing agents in the method of the present invention:

Example 1

---

Starting Materials:

$$CH_3-\overset{\overset{CH_3}{|}}{N}-CH_2-CH_2-NH_2, \text{ N,N,-Dimethylethylenediamine, 95\%}$$
111.4 gm (1.2 moles).

2-adamantanone, 99%: 151.7 gm (1.0 mole).
Solvent: cyclohexane: 30 ml
Temperature: The pot temperature was kept at about 80° C. and
water was azeotroped out at 69° C.

Products:

| Product | Yield, % | $^{13}C$ NMR | Elemental Analysis |
|---|---|---|---|
| [adamantyl]=N-CH2-CH2-N(CH3)2 | 100 | 180.7, 60.9, 48.3, 46.0, 43.9, 39.3, 38.5, 36.7, 33.4, 28.0 | — |
| [adamantyl]-NH-CH2-CH2-N(CH3)2 | 100 | 62.3, 60.9, 48.3, 45.7, 38.2, 37.8, 32.3, 31.5, 28.0, 27.7 | — |

| Product | Yield, % | ¹³C NMR | Elemental Analysis |
|---|---|---|---|
| [structure: 2-adamantyl-N(CH₃)-CH₂CH₂-N(CH₃)₂] | 90 | 67.7, 56.6, 52.4, 46.4, 39.8, 38.2, 37.7, 31.7, 30.0, 27.8, 27.6 | — |
| [structure: 2-adamantyl-N(CH₃)-CH₂CH₂-N⁺(CH₃)₃ I⁻] | 90 | 69.3, 63.3, 54.4, 48.5, 41.5, 40.2, 39.7, 33.5, 31.9, 29.2 (2 types) | Calculated for C₁₆H₃₁N₂I: C: 50.79; H: 8.26; N: 7.40; I: 33.54 Found: C: 51.13; H: 8.23; N: 7.38; I: 33.81 |
| [structure: 2-adamantyl-N⁺(CH₃)₂-CH₂CH₂-N⁺(CH₃)₃ 2I⁻] | 86 | 83.0, 61.4, 59.7, 57.4, 54.5, 42.8, 39.9, 34.2, 31.7, 29.9, 28.7 | Calculated for C₁₇H₃₄N₂I₂: C: 39.25; H: 6.59; N: 5.38; I: 48.79 Found: C: 39.02; H: 6.40; N: 5.34; I: 48.23 |

*Yield based on 2-adamantanone

Example 2

Starting Materials:

$H_2N-CH_2-CH_2-\overset{H}{\underset{|}{N}}-CH_2-(CH_2)-NH_2$, Diethylenediamine (99%): 104.2 gm (1 mole).

2-adamantanone, (99%): 333.8 gm (2.2 moles).
Solvent: Toluene: 30 ml.
Temperature: Reflux.
Products:

| Product | Yield, % | ¹³C NMR | Elemental Analysis |
|---|---|---|---|
| [bis(2-adamantylidene=N-CH₂CH₂-)NH] | 100 | 181.1, 50.8, 49.6, 43.9, 39.4, 38.4, 36.7, 33.5, 27.6 | — |
| [bis(2-adamantyl-NH-CH₂CH₂-)NH] | 95 | 62.1, 50.1, 46.8, 38.1, 37.7, 32.3, 31.5, 28.0, 27.8 | — |
| [bis(2-adamantyl-N(CH₃)-CH₂CH₂-)N-CH₃] | 90 | 68.6, 54.9, 52.1, 43.9, 39.9, 38.7, 38.2, 31.6, 30.0, 27.8, 27.5 | — |
| [bis(2-adamantyl-N(CH₃)-CH₂CH₂-)N⁺(CH₃)₂ I⁻] | 86 | 69.0, 61.6, 52.1, 49.7, 38.5, 37.7, 37.5, 32.1, 30.0, 27.5, 27.4 | Calculated for C₂₈H₅₀N₃I: C: 60.53; H: 9.07; N: 7.56; I: 22.84 Found: C: 60.62; H: 9.05; N: 7.64; I: 23.4 |

-continued

| Structure | Yield | 13C NMR | Elemental Analysis |
|---|---|---|---|
| [adamantyl-N+(CH3)2-CH2CH2-N+(CH3)2-CH3]2 · 3I− | 54 | 85.1, 62.9, 60.2, 55.5, 55.3, 43.6, 40.6, 34.8, 32.7, 30.6, 29.4 | Calculated for $C_{30}H_{56}N_3I_3$: C: 42.92; H: 6.72; N: 5.00; I: 45.35 Found: C: 42.73; H: 7.08; N: 5.03; I: 45.43 |

*Yield based on diethylenetriamine.

Example 3

Starting Materials:

$H_2N-CH_2-CH_2$
$H_2N-CH_2-N$ , Tris(2-aminoethyl)amine, 99%: 147.7 gm (1 mole).
$H_2N-CH_2-CH_2$ 2-adamantanone, 99%: 500.7 gm (3.3 moles)
Solvent: Toluene: 30 ml
Temperature: Reflux
Products:

| Product | Yield, % | 13C NMR | Elemental Analysis |
|---|---|---|---|
| (adamantyl=N-CH2CH2-)3N | 100 | 180.8, 56.2, 48.2, 43.9, 39.3, 37.5, 33.4, 30.1, 27.9 | — |
| (adamantyl-NH-CH2CH2-)3N | 94 | 62.3, 55.0, 44.9, 38.1, 37.7, 32.3, 31.5, 28.0, 27.8 | — |
| (adamantyl-N(CH3)-CH2CH2-)3N | 72 | 67.3, 52.1, 52.1, 39.7, 38.0, 37.5, 31.5, 29.9, 27.7, 27.4 | Calculated for $C_{36}H_{60}N_4$: C: 78.78; H: 11.02; N: 10.20 Found: C: 78.88; H: 11.01; N: 10.26 |
| [adamantyl-N+(CH3)2-CH2CH2-]2N+(CH3)-... · 3I− | 53 | — | Calculated for $C_{30}H_{56}N_3I_3$: C: 42.92; H: 6.72; N: 5.00; I: 45.35 Found: C: 42.73; H: 7.08; N: 5.03; I: 45.43 |

*Yield based on tris(2-aminoethyl)amine.

Example 4

Starting Materials:
$HN_2-(CH_2)_6-NH_2$, 1,6-diaminohexane, 98%: 118.6 gm (1 mole).
2-adamantanone, 99%: 333.8 gm (2.2 moles).
Solvent: Toluene: ≈30 ml
Temperature: Reflux
Products:

| Product | Yield, % | 13C NMR | Elemental Analysis |
|---|---|---|---|
| (adamantyl=N-(CH2)3-)2 | 100 | — | — |

-continued

| Product | Yield, % | 13C NMR | Elemental Analysis |
|---|---|---|---|
| 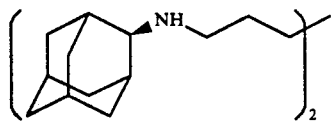 | 95 | 62.0, 47.2, 38.1, 37.8, 32.2, 31.5, 30.7, 28.0, 27.8 27.6 | — |
| 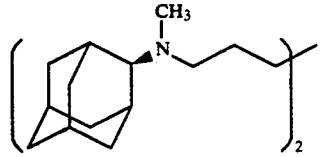 | 90 | 66.9, 53.7, 39.0, 38.0, 37.6, 31.5, 29.8, 27.8, 27.7, 27.5, 24.9 | — |
| 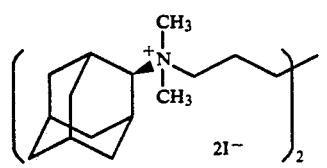 | 83 | 82.1, 69.1, 54.6, 43.7, 40.9, 35.0, 32.5, 30.8, 29.6, 29.1, 25.9 | Calculated for $C_{30}H_{54}N_2I_2$: C: 51.73; H: 7.82; N: 4.02; I: 36.44 Found: C: 51.24; H: 7.91; N: 3.80; I: 36.67 |

*Yield based on 1,6-diaminohexane.

Example 5

Starting Materials:

$$H_3C-\overset{\overset{CH_3}{|}}{N}-CH_2-CH_2-CH_2-NH_2,$$ N,N-Dimethylpropylenediamine, 100%:
122.6 gm (1.2 moles)

2-Adamantanone, 99%: 150.7 gm (1 mole).

Solvent: Cyclohexane: ≈30 ml

Temperature: The pot tempeature was 85° C. Water azeotroped out at 69° C.

| Product | Yield, % | 13C NMR | Elemental Analysis |
|---|---|---|---|
| 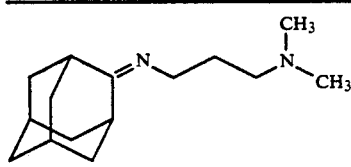 | 97 | 179.9, 58.1, 47.9, 45.7, 43.9, 39.3, 38.4, 36.6, 33.0, 29.5, 27.9 | — |
| 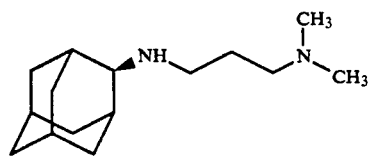 | 97 | 62.3, 58.8, 46.0, 45.9, 38.4, 38.0, 32.3, 31.6, 28.9, 28.1, 27.9 | — |
| 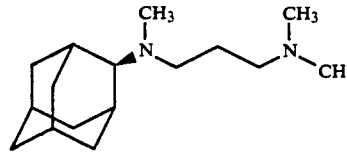 | 74 | 67.3, 58.7, 52.1, 46.0, 39.1, 38.2, 37.8, 31.7, 29.9, 27.8, 27.6, 23.7 | — |
| 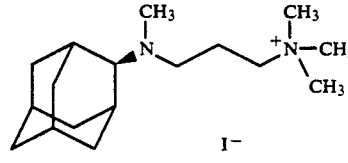 | 69 | 71.0, 68.8, 57.1, 53.4, 42.2, 40.9, 40.7, 34.3, 32.4, 30.4(2 types of carbons), 20.8 | — |

| | | | |
|---|---|---|---|
| 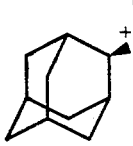 | 70 | 83.1, 66.6, 64.4, 57.4, 54.6, 43.4, 40.6, 34.7, 32.2, 30.5, 29.2, 21.0 | Calculated for $C_{18}H_{36}N_2I_2$: C: 40.46; H: 6.79; N: 5.24; I: 47.50 Found: C: 40.09; H: 6.89; N: 5.19; I: 48.15 |

*Yield based on 2-adamantanone.

Examples 6–33

Examples 6–33 demonstrate the inorganic porous solid synthesis method of the invention.

Four starting mixtures containing the aluminum source were used:

| Starting Mixture I | Starting Mixture II |
|---|---|
| $SiO_2/Al_2O_3 = 10$ | $SiO_2/Al_2O_3 = 20$ |
| $NaAlO_2$: 12.24 gm | $NaAlO_2$: 6.07 gm |
| NaOH: 4.39 gm | NaOH: 7.37 gm |
| $H_2O$ (deionized): 187.74 gm | $H_2O$ (deionized): 187.07 gm |
| $SiO_2$ sol (30%): 96 gm | $SiO_2$ sol (30%): 96 gm |
| Starting Mixture III | Starting Mixture IV |
| $SiO_2/Al_2O_3 = 40$ | $SiO_2Al_2O_3 = 80$ |
| $NaAlO_2$: 3.04 gm | $NaAlO_2$: 1.52 gm |
| NaOH: 8.87 gm | NaOH: 9.61 gm |
| $H_2O$ (deionized): 185.41 gm | $H_2O$ (deionized): 185.04 gm |
| $SiO_2$ sol (30%): 96 gm | $SiO_2$ sol (30%): 96 gm |

In Examples 6–33 template (predetermined amount) was added to a starting mixture. Because the templates were not completely soluble in the starting mixture even at boiling, the template and the mixture were heated to near boiling and homogenized in a Waring blender. To this homogenized mixture in the Waring blender were added 96.0 gm $SiO_2$ Sol, and the final mixture was again homogenized. The homogenized final mixture, which had the appearance of whipped cream, was then transferred into a 600 ml Parr reactor. The rector was equipped with a heater, a stirrer, a nitrogen inlet and a sampling outlet. After closing the reactor, it was pressurized with nitrogen (500 psig for sampling), it was heated to a temperature with stirring. When the temperature was reached, the stirrer was turned off and the mixture was allowed to age for 1 day. The mixture was aged at elevated temperature because the solubility of the template is higher at higher temperature. After the static aging, the stirrer was turned on. Samples were taken periodically to detect crystallization by powder x-ray diffraction. The reaction was terminated when crystallization of the zeolite had occurred.

The following examples illustrate the conditions and templates which favor the crystallization of ECR-1.

| Example | Template n | Feed $SiO_2/Al_2O_3$ | Reaction Temp C. | Total Time Days | $SiO_2/Al_2O_3$ | alpha | Product |
|---|---|---|---|---|---|---|---|
| 6 | 2 | 20 | 160 | 10 | 11.7 | — | Mordenite |
| 7 | 3 | 20 | 160 | 7 | — | — | Mordenite |
| 8 | 3 | 40 | 160 | 7 | — | — | Mordenite |
| 9 | 3 | 80 | 160 | 7 | — | — | Mordenite |
| 10 | 4 | 10 | 120 | 5 | 7.2 | — | Mordenite + Analcime |
| 11 | 4 | 10 | 160 | 5 | 8.9 | — | Mordenite + Analcime |
| 12 | 4 | 20 | 160 | 6 | — | — | Mordenite |
| 13 | 5 | 10 | 160 | 12 | 7.5 | — | Anacime + Mordenite ECR-1 |
| 14 | 5 | 20 | 160 | 7 | 9.7 | 627 | ECR-1 + Mordenite |
| 15 | 5 | 80 | 160 | 7 | 30.4 | — | Mordenite + ECR-1 |
| 16 | 6 | 10 | 120 | 18 | 7.6 | — | Analcime + ECR-1 |
| 17 | 6 | 10 | 120 | 14 | 7.7 | — | ECR-1 |
| 18 | 6 | 20 | 160 | 6 | 9.9 | 750 | ECR-1 + Mordenite |
| 19 | 7 | 10 | 140 | 7 | 6.5 | 336 | ECR-1 + Analcime |
| 20 | 7 | 10 | 160 | 7 | 7.7 | 795 | ECR-1 + Analcime |
| 21 | 7 | 20 | 160 | 7 | 9.8 | 353 | Mordenite + ECR -1 |
| 22 | 7 | 80 | 160 | 7 | 30.9 | — | Mordenite |
| 23 | 8 | 10 | 140 | 7 | 7.6 | — | ECR-1 + Analcime |
| 24 | 8 | 10 | 160 | 5 | 7.5 | 736 | ECR-1 |
| 25 | 8 | 20 | 160 | 7 | 10.5 | 597 | Mordenite |
| 26 | 9 | 10 | 140 | 10 | 7.0 | — | ECR-1 + Analcime |
| 27 | 9 | 20 | 160 | 7 | 10.3 | 1182 | Mordenite + ECR-1 |
| 28 | 9 | 40 | 160 | 7 | 13.7 | — | Mordenite |
| 29 | 10 | 10 | 140 | 9 | 7.5 | — | ECR-1 |

-continued

| Example | Template n | Feed SiO2/Al2O3 | Reaction Temp C. | Total Time Days | SiO2/Al2O3 | alpha | Product |
|---|---|---|---|---|---|---|---|
| 30 | 10 | 10 | 160 | 9 | 8.9 | — | ECR-1 Mordenite Analcime |
| 31 | 10 | 10 | 160 | 5 | 7.5 | — | ECR-1 + Mordenite |
| 32 | 10 | 20 | 160 | 5 | — | — | Mordenite |
| 33 | 12 | 10 | 140 | 6 | 7.8 | 527 | Mazzite |

Changes and modifications in the specifically described embodiments can be carried out without departing from the scope of the invention which is intended to be limited only by the scope of the appended claims.

What is claimed is:

1. A method for synthesizing a porous inorganic solid comprising the steps of:
   (a) forming a reaction mixture containing water, an alumina source, a silica source, an alkali metal oxide source, and a diquaternary ammonium salt having the formula:

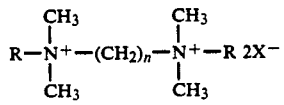

wherein R is a diamondoid group, n is from about 1 to about 50, and X is an anion which is not detrimental to the formation of said porous inorganic solid; and
   (b) recovering a porous inorganic solid from said reaction mixture of step (a).

2. The method of claim 1 wherein X is selected from the group consisting of halogen and hydroxide groups.

3. The method of claim 1 further comprising crystallizing said porous inorganic solid in the absence of added nucleating seeds to form a product selected from the group consisting of ECR-1, mordenite, or analcime.

4. The method of claim 1 wherein said reaction mixture is further characterized by the following molar ratios of oxides:

| | |
|---|---|
| SiO2/Al2O3: | 10 to 80 |
| H2O/SiO2: | 30 to 90 |
| R/SiO2: | 0.05 to 0.10, |

5. The method of claim 1 wherein n is from about 1 to about 20.

6. The method of claim 5 wherein in is from about 2 to about 12.

7. A method for synthesizing a crystalline material comprising the steps of:
   (a) forming a reaction mixture containing water, an alumina source, a silica source, an alkali metal oxide source, and a diquaternary ammonium salt having the formula:

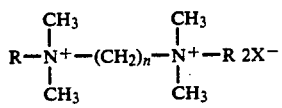

wherein R is a diamondoid group, n is from about 1 to about 50, and X is an anion which is not detrimental to the formation of said crystalline material; and
   (b) crystallizing product selected from the group consisting of materials having the structure of ECR-1, mordenite, or analcime from said reaction mixture of step (a) in the absence of added seed crystals.

8. The method of claim 7 wherein said reaction mixture is further characterized by the following molar ratios of oxides:

| | |
|---|---|
| SiO2/Al2O3: | 10 to 80 |
| H2O/SiO2: | 30 to 90 |
| R/SiO2: | 0.05 to 0.10. |

9. The method of claim 8 wherein n is from about 3 to about 10.

10. The method of claim 9 further comprising controlling reaction temperature at from about 120° to about 180° C.

11. The method of claim 10 further comprising recovering a crystalline microporous material from said reaction mixture, said crystalline microporous material having the structure of ECR-1 as defined herein.

12. The method of claim 7 wherein X is selected from the group consisting of halogen and hydroxide groups.

* * * * *

UNITED STATES PATENT AND TRADEMARK OFFICE
CERTIFICATE OF CORRECTION

PATENT NO. : 5,256,391

DATED : October 26, 1993

INVENTOR(S) : C.S.H. Chen et al.

It is certified that error appears in the above-identified patent and that said Letters Patent is hereby corrected as shown below:

Col. 20, line 51, delete "as defined herein"

Col. 19, line 51, delete "," and insert --.-- after "0.10"

Signed and Sealed this

Twenty-seventh Day of September, 1994

Attest:

BRUCE LEHMAN

*Attesting Officer*   *Commissioner of Patents and Trademarks*